United States Patent
Asanov et al.

(10) Patent No.: US 6,511,854 B1
(45) Date of Patent: Jan. 28, 2003

(54) REGENERABLE BIOSENSOR USING TOTAL INTERNAL REFLECTION FLUORESCENCE WITH ELECTROCHEMICAL CONTROL

(75) Inventors: Alexander N. Asanov, Starkville, MI (US); W. William Wilson, Starkville, MI (US); Philip B. Oldham, Starkville, MI (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/463,800

(22) PCT Filed: Jul. 30, 1997

(86) PCT No.: PCT/US97/13500

§ 371 (c)(1),
(2), (4) Date: Jun. 12, 2000

(87) PCT Pub. No.: WO99/06835

PCT Pub. Date: Feb. 11, 1999

(51) Int. Cl.[7] .............................................. G01N 33/543
(52) U.S. Cl. .................... 436/518; 356/300; 356/318; 385/12; 385/129; 385/130; 385/131; 422/55; 422/82.05; 422/82.11; 435/6; 435/7.1; 435/7.2; 435/7.4; 435/7.5; 435/182; 435/287.1; 435/287.2; 435/287.9; 435/288.7; 435/808; 436/164; 436/165; 436/504; 436/524; 436/525; 436/527; 436/805
(58) Field of Search ...................... 435/6, 7.1, 7.2, 435/7.4, 7.5, 7.92, 182, 287.1, 287.2, 287.9, 288.7, 808; 436/164, 165, 504, 518, 524, 525, 527, 535, 805, 804; 422/55, 82.05, 82.11; 385/12, 129, 130, 131; 356/300, 318

(56) References Cited

U.S. PATENT DOCUMENTS

| | | | | |
|---|---|---|---|---|
| 4,775,637 A | * | 10/1988 | Sutherland et al. | 436/527 |
| 5,135,876 A | * | 8/1992 | Andrade et al. | 436/518 |
| 5,143,066 A | | 9/1992 | Komives et al. | |
| 5,156,810 A | | 10/1992 | Ribi | |
| 5,192,502 A | * | 3/1993 | Attridge et al. | 422/57 |
| 5,492,840 A | * | 2/1996 | Malmqvist et al. | 436/518 |
| 5,631,170 A | * | 5/1997 | Attridge | 436/518 |
| 5,750,410 A | * | 5/1998 | Dou et al. | 436/525 |
| 5,811,312 A | * | 9/1998 | Hasegawa et al. | 436/527 |
| 5,965,456 A | * | 10/1999 | Malmqvist et al. | 436/514 |

* cited by examiner

*Primary Examiner*—Christopher L. Chin
(74) *Attorney, Agent, or Firm*—TraskBritt, P.C.

(57) ABSTRACT

An improved electrochemical method for disassociating a biological binding partner from a corresponding second biological binding partner associated with a waveguide surface, the electrochemical method involving the application of an electrical potential to said waveguide surface (118), the improvement comprising: applying the electrical potential to the waveguide surface (118) as a square wave polarization function. Preferably, the waveguide surface is comprised of indium tin oxide. The biological binding partners are selected from the group consisting of antigen-antibody, avidin-biotin, enzyme-substrate, cell receptor-substrate/analog, antibody/anti-antibody, DNA, RNA, and fragments thereof. The antigen may be comprised of an epitope. The epitope is produced by a solid phase peptide synthesis performed on said waveguide surface (118).

8 Claims, 7 Drawing Sheets

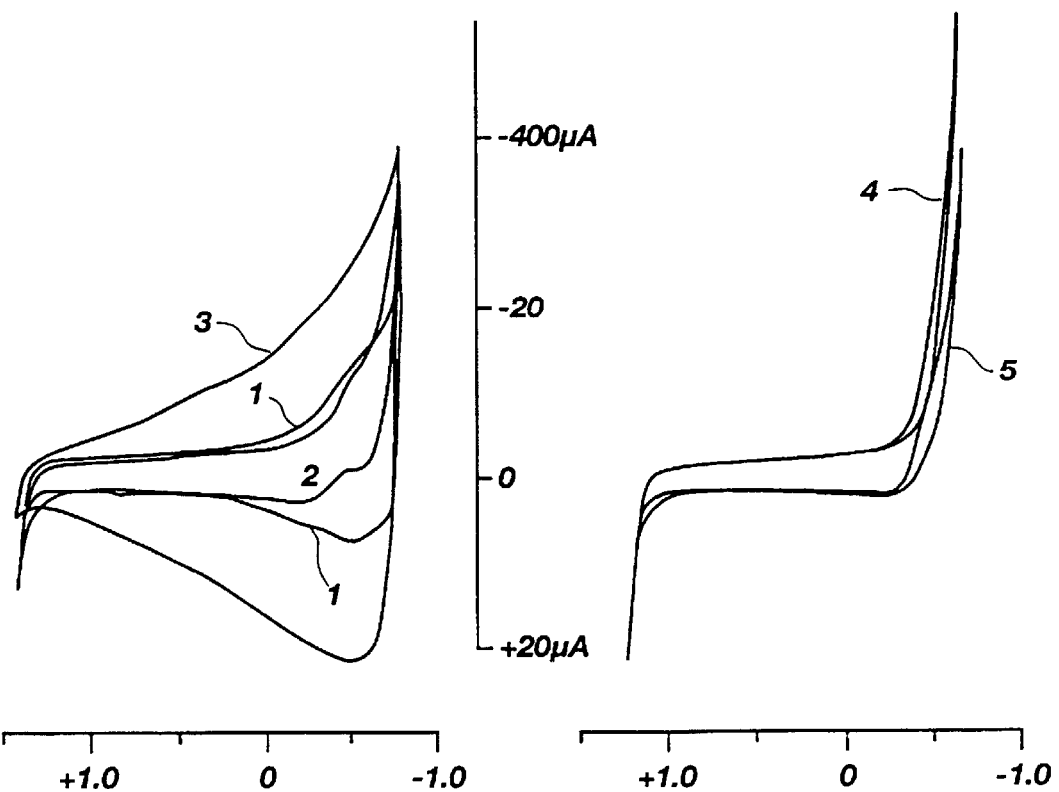

REGENERABLE BIOSENSOR USING TOTAL INTERNAL REFLECTION FLUORESCENCE WITH ELECTROCHEMICAL CONTROL

TECHNICAL FIELD

This invention relates generally to a diagnostic apparatus and to related methods for using that apparatus in rapidly analyzing samples for analytes of interest, and more particularly to an apparatus and associated methods which provide simultaneous fluorescence detection and electrochemical control of biospecific binding.

BACKGROUND

Investigation of the interactions between biomolecules has attracted increasing attention in recent years. An understanding of these interactions and the ability to control them are critical for a variety of objectives, such as the determination of structure-function relationships and protein crystallogenesis, drug design and development of targeted drug delivery systems, and biomolecular engineering and design of biosensors.

Total internal reflection fluorescence (hereinafter "TIRF") techniques have proven to be well-suited for investigating biomolecular interactions. Such techniques generally utilize optical waveguides, either planar or cylindrical, having a portion of one surface of the waveguide carrying an immobilized binding agent, such as a specific binding partner (e.g., an antibody or antibody fragment). A light beam is introduced into the waveguide wherein the light beam travels in the waveguide. The light beam is totally internally reflected at the interface between the waveguide and a surrounding medium having a lower refractive index than the waveguide. A portion of the electromagnetic field of the internally reflected light beam penetrates into the surrounding medium and forms an evanescent light field. The intensity of evanescent light drops off substantially exponentially with increasing distance from the waveguide surface. In a fluoro-immunoassay, evanescent light can be used to selectively excite tracer molecules directly or indirectly bound to the immobilized binding agent, while tracer molecules free in solution beyond the evanescent light penetration distance are not excited and thus do not contribute "background" fluorescence. The use of evanescent field properties for fluorescence measurements is sometimes referred to as evanescent sensing. For a glass or a similar silica-based material, or an optical plastic such as polystyrene, with the surrounding medium being an aqueous solution, the region of effective excitation by evanescent light generally extends about 1000 to 2000 Å (angstroms) from the waveguide surface. This depth is sufficient to excite most of the tracer molecules bound to the capture molecules (antibodies, receptor molecules, and the like, or fragments thereof) on the waveguide surface, without exciting the bulk of the tracer molecules that remain free in solution. The resulting fluorescence reflects the amount of tracer bound to the immobilized capture molecules, and in turn the amount of analyte present in the aqueous solution.

The fluorescent light from the tracer molecules will conversely also evanescently penetrate back into the waveguide and be propagated therein. The maximum solution depth for efficient evanescent collection by the waveguide approximates the depth of the region of evanescent penetration into the solution, and thus the waveguide-penetrating portion of the tracer fluorescence can also be used to selectively measure fluorescence from tracer bound to the waveguide surface.

U.S. Pat. No. RE 33,064 to Carter, U.S. Pat. No. 5,081,012 to Flanagan et al, U.S. Pat. No. 4,880,752 to Keck, U.S. Pat. No. 5,166,515 to Attridge, and U.S. Pat. No. 5,156,976 to Slovacek and Love, and EP publication Nos. 0 517 516 and 0 519 623, both by Slovacek et al, all disclose apparatus for fluoro-immunoassays utilizing evanescent sensing principles.

Although TIRF immunosensors achieve high sensitivity, they also have poor reversibility (i.e., poor regeneration of the sensing surface from the difficulty of removing the analyte of interest from the capture molecules). Quantitative analytical measurements performed with immunosensors require either regeneration of the sensing surface or quantization based on a series of measurements with disposable units. Unfortunately, highly sensitive biosensors generally require high affinity biospecific interactions which makes regeneration difficult. More specifically, association rate constants for most antibodies, $k_a$, have been shown to vary no more than one order of magnitude. However, the dissociation constants, $k_d$, may vary a thousandfold. Therefore, the affinity constant, $K_f = k_a/k_d$, is determined primarily by the $K_d$ value rather than by $K_a$. Additionally, surface immobilization of the immunoassay typically results in a decreased dissociation rate constant. Thus, a sensitive immunosensor with a large $K_a$, is commonly not a true linear sensor but rather a simple binary detector (i.e., analyte present/analyte not present), since it cannot respond rapidly to changes in analyte concentration.

The regeneration of the sensing surface is important in order to reduce testing costs; however, regeneration is a difficult task. Regeneration techniques can involve use of extreme pH (either high or low), high temperatures, and/or chaotropic agents to dissociate an antibody-antigen complex from the sensing surface. Unfortunately, such extreme treatment often results in a significant loss of biospecific activity. Thus, the most sensitive biosensors are disposable devices and quantization is typically obtained using multiple single use sensors.

An example of total kinetic irreversibility is given by the biotin-avidin bond which is among the strongest non-covalent biospecific interactions known. The affinity constant ($K_f$) of biotin-avidin in solution has been reported as high as about $10^{15}$ M$^{-1}$. To date, biotin-avidin technology provides an advanced versatile tool for designing types of biosensors. However, systems based on biotin-avidin interactions are inherently single use devices (with respect to the biotin-avidin bond), since the biotin-avidin complex is stable to extreme pH, extreme temperature, and even resistant to chaotropic agents which makes the complex almost impossible to regenerate.

Investigations by one inventor of the present invention used a TIRF flow cell equipped with a transparent $SnO_2$ electrode to demonstrate the capability of electrochemical polarization to stimulate desorption of irreversibly adsorbed protein. (see Asanov, et al., "Electrochemical Control of Protein Interactions with Solid Surfaces", *Charge and Field Effects in Biosystems*, pp. 14–28 (eds. Milton J. Allen et al. (Birkhauser, Inc., Boston, Mass. 1992)). It was found that electrochemical polarization imposed by steps was more efficient for surface regeneration in protein adsorption experiments than slow linear electrochemical polarization changes, over the same voltage range. This approach has been adapted for regeneration of a TIRF immunosensor surface, as well as, to stimulate dissociation of streptavidin bound to a biotinylated surface. However, this approach was still not sufficiently effective to make a sufficiently reversible immunosensor for standard use.

Therefore, it would be advantageous to develop an apparatus and method for regeneration of an immunosensor surface having a high affinity constant between the immobilized binding agent and the analyte of interest.

DISCLOSURE OF THE INVENTION

The present invention relates to an apparatus and methods which provide simultaneous fluorescence detection and electrochemical control of biospecific binding. In particular, the invention involves a highly sensitive and reversible biosensor which regulates complex binding (e.g., antibody-antigen, interacting nucleotides, enzyme-substrate, streptavidin-biotin interactions, etc.) so as to render the biosensor reusable.

The biosensor may be constructed by covalently binding biotin to a transparent electrode, preferably indium tin oxide (hereinafter "ITO") or other (e.g., $Sn_2O$ or zinc oxide) transparent electrode, wherein the electrode also serves as an integral part of a TIRF flow cell. The TIRF flowcell is used to monitor biospecific interactions and electrochemical polarization is employed to control interactions between, for example, biotin and streptavidin or between biotin and anti-biotin antibodies. Both streptavidin and polygonal anti-biotin antibodies are bound kinetically irreversibly to the biotinylated surface of the working electrode.

Without application of the invention, the assay exhibits an extremely slow release of the bound analytes, causing poor regeneration capability of the biosensor surface (i.e., the biotinylated surface). However, electrochemical polarization was used to stimulate dissociation of kinetically irreversibly bound biotin-streptavidin and antibody-antigen complexes. It has been found that a "square wave" polarization function stimulated dissociation surprisingly more effectively than a "saw tooth"function over the same voltage range. A square wave function is an oscillation of the amplitude which shows periodic discontinuities between two values, remaining constant between jumps. Application of the square wave polarization results in regeneration of an active biotinylated surface. Electrochemical polarization also modified affinity and kinetics of protein adsorption which could likely be used to promote biospecific interactions and/or to suppress nonspecific adsorption.

Methods of making and using the biosensor are also included within the invention.

BRIEF DESCRIPTION OF THE FIGURES

While the specification concludes with claims particularly pointing out and distinctly claiming that which is regarded as the present invention, the advantages of this invention can be more readily ascertained from the following description of the invention when read in conjunction with the accompanying drawings in which:

FIGS. 4 and 5 illustrate cyclic voltammograms of bare and chemically modified ITO electrodes of the present invention;

BEST MODE OF THE INVENTION

Figure 1:
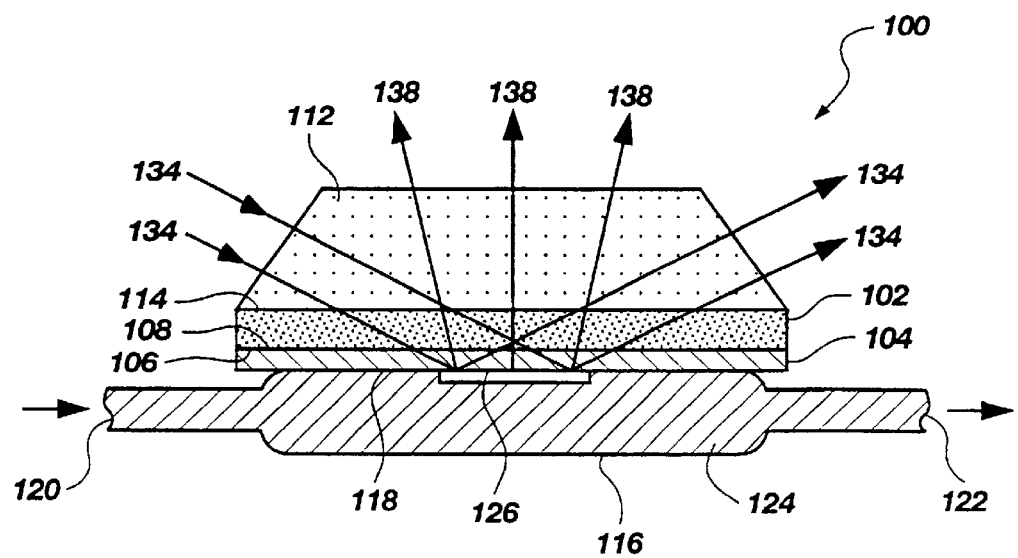
FIGS. 1 and 2 are illustrations of a TIRF flowcell of the present invention.
Figure 2:
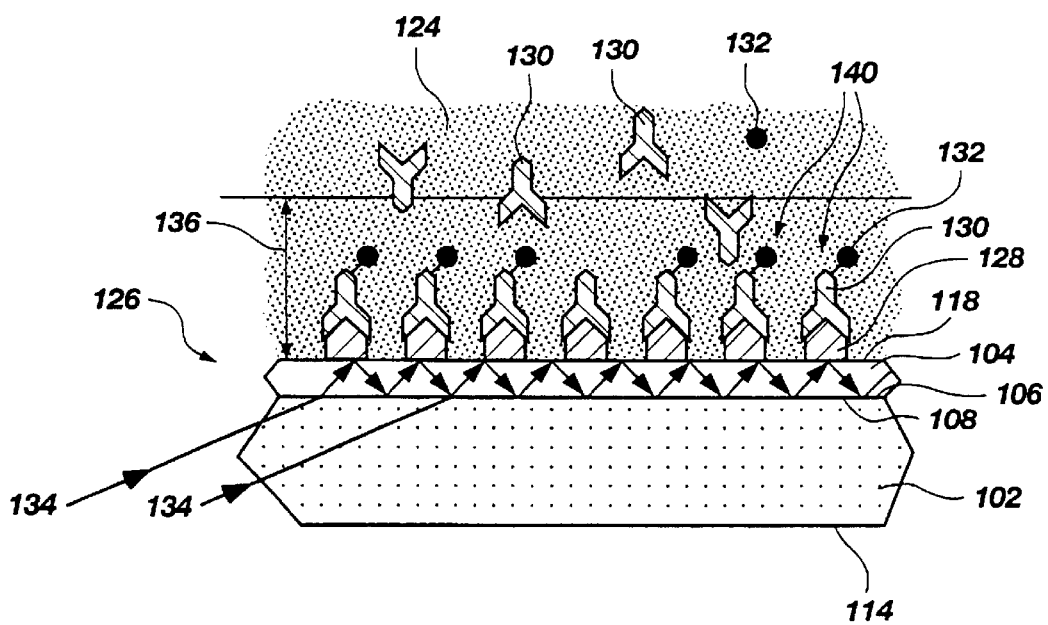
Figure 3:
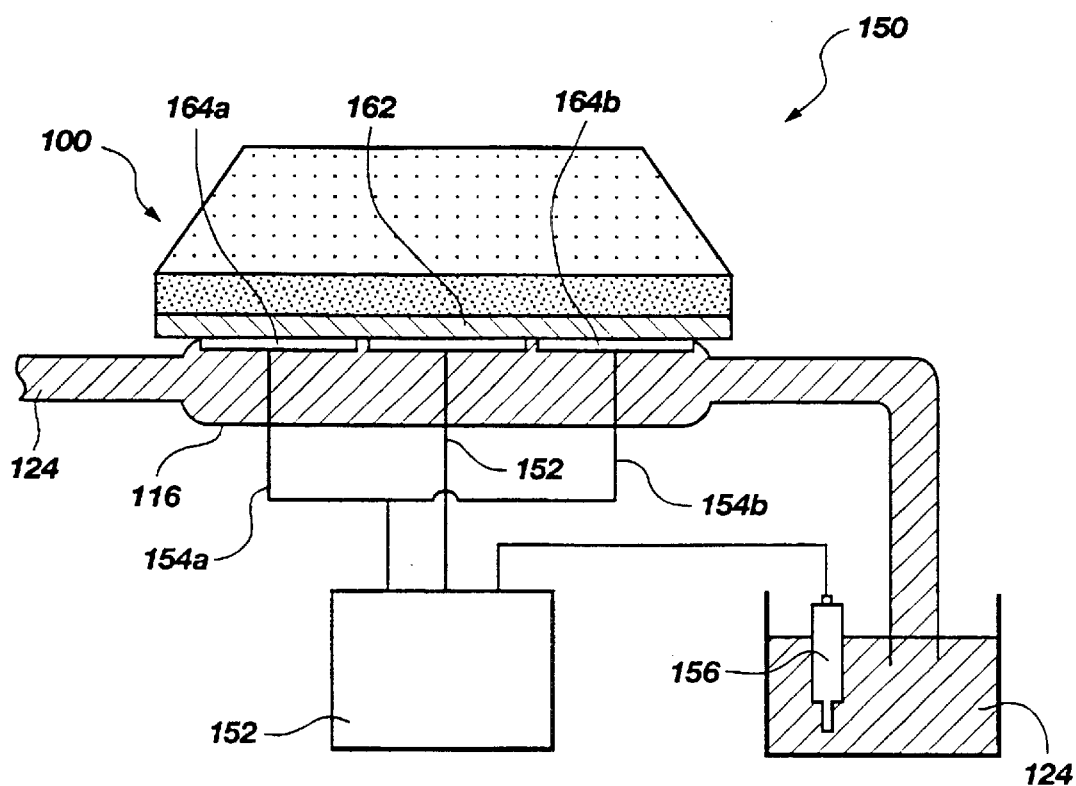
FIG. 3 illustrates a TIRF flowcell in combination with a 3-electrode electrochemical system of the present invention.

FIGS. 1 and 2 illustrate a TIRF flowcell 100, or a portion thereof, of the present invention. It should be understood that FIGS. 1–3 presented in conjunction with this description are not meant to be actual views of any particular portion of an actual immunosensor device, but are merely idealized representations which are employed to more clearly and fully depict the apparatus and process of the invention than would otherwise be possible.

The TIRF flowcell 100, shown in FIG. 1, comprises a planar translucent substrate 102, such as a quartz slide, with a light transmissive waveguide 104, preferably comprising ITO, attached by a first surface 106 to a first surface 108 of the substrate 102 and a prism 112 is placed over a second surface 114 of the substrate 102. A flow chamber 116 extends from a second surface 118 of the waveguide 104, wherein the waveguide 104 comprises one wall of the flow chamber 116. The flow chamber 116 includes an inlet 120 and an outlet 122 for delivering a test sample solution 124 into and out of the flow chamber 116.

The waveguide second surface 118 also includes at least one binding agent area 126. This binding agent area 126 is shown on a larger scale in FIG. 2. The binding agent area 126 comprises a plurality of individual immobilized binding agents 128, preferably covalently bonded biotin, attached to the waveguide second surface 118. FIG. 2 illustrates complexes 140 of antibodies of interest 130 and fluorescent tracer molecules 132. The complexes 140 are attached to the binding agents 128. Light beams 134 are introduced into the waveguide 104 through the prism 112, as shown in FIG. 1. The light beams 134 travel in the waveguide 104, wherein the light beams 134 are totally internally reflected at the interface between the waveguide first surface 106 and the substrate first surface 108, as well as the interface between the waveguide second surface 118 and the test sample solution 124, as shown in FIG. 2.

A portion of an electromagnetic field of the internally reflected light beams 134 penetrates into the surrounding medium and forms an evanescent light field 136, approximate 300 nm deep into the test sample solution 124. The intensity of evanescent light within the evanescent light field 136 drops off substantially exponentially with increasing distance from the waveguide second surface 118. The evanescent light field 136 excites the fluorescent tracer molecules 132 bound to the immobilized antibodies 130, while fluorescent tracer molecules 132 free in solution beyond the evanescent light penetration distance are not excited and thus do not contribute "background" fluorescence.

Resulting fluorescence 138 travels through the waveguide 104, substrate 102, and out the prism 112 where it can be measured, as shown in FIG. 1. The resulting fluorescence 138 is an indication of the amount of fluorescent tracer molecules 132 bound to the immobilized antibodies 130 (complex 140). The assay format shown in FIG. 2 is an indirect immunoassay format wherein the antibodies 130 of interest in the test sample solution 122 replace previously bound complexes 140. Thus, the presence of antibodies 130 in the test sample solution 122 is detected by a decrease of the fluorescence signal.

EXAMPLE

The TIRF flowcell 100 was combined with a 3-electrode electrochemical system 150 for TIRF-electrochemistry (TIRF-EC) experiments, as shown in FIG. 3. The TIRF flowcell 100 was used in conjunction with a SLM-Aminco (Rochester, N.Y.) AB-2 spectrofluorometer to detect and measure fluorescence (not shown). The electrochemical system 150 consists of a controller 160, i.e., a BAS cyclic voltammograph model CV-27 (Bioanalytical Systems, Inc., West Lafayette, Ind.). The controller 160 comprises a working electrode 152, two auxiliary electrodes 154a and 154b, and a reference electrode 156. The working electrode 152 and the auxiliary electrode 154 potentials are measured relative to the reference electrode 156, preferably a saturated Ag/AgCl reference electrode in a container 158 receiving the test sample solution 124 flowing out of the TIRF flowcell flow chamber 116.

It has been found that the transport of the analyte of interest (e.g., antibodies 128 of FIG. 2) to and from the binding agent area 126 is a critical aspect of the electrochemical system 150. In a preferred embodiment, the system uses biotin-avidin and antibody-antigen interactions. However, since the association process for biotin-avidin and antibody-antigen interactions is extremely rapid, reassociation of any unbound analyte of interest after disrupting these bonds occurs if the diffusive and/or convective flow of the sample test solution 124 des not remove the analyte of interest from the binding agent area 126. Therefore, a specialized fluid transport system (not shown) was devised, wherein gravity flows of test sample solutions 124 and pure buffer solution were directed into the TIRF flowcell flow chamber 116 by polytetrafluoroethylene tubing (not shown) and were valved/switched by a polytetrafluoroethylene 3-way valve (not shown). The dead volume of the fluid transport system was approximately 10 $\mu$L, while the volume of the TIRF flowcell flow chamber 116 (1 cm×2 cm×0.015 cm) was approximately 30 $\mu$L. A relatively high wall shear rate, y, given by equation [1], was attained in the flow chamber with width, w=1 cm, at a volumetric flow rate, V, of 10 mL/min, wherein b is the thickness of the flow chamber 116:

$$\gamma = 6V/wb^2 = 4400 \text{ s}^{-1} \quad [1]$$

At this shear rate, convection and diffusion establish a steady state concentration profile of the analyte of interest at the waveguide second surface 118 within a short time, $\tau$ (transient time), as given by equation [2]:

$$\tau = 3L^{2/3} \gamma^{-2/3} D^{-3/4} \quad [2]$$

where L is the distance from the flow chamber entrance and D is the translational diffusion coefficient of IgG. When the L is 2 cm and D is $4 \times 10^{-7}$ cm$^2$ sec$^{-1}$ (as with the present example), the steady state profile of the IgG concentration develops during the transient time of approximately 4 seconds.

Since the translational diffusion coefficient of streptavidin is greater than that of IgG, the transient time for the streptavidin used in this example is less than 4 seconds. After the transient time period, the concentration profile has a substantially uniform cross-section within the TIRF flowcell flow chamber 116 and diffusion-convection provides fast transport of the analyte of interest to (i.e., antibodies 130) and from the waveguide second surface 118. It has been found that the transient time of the electrochemical system 150 does not exceed 4 seconds at a solution flow rate greater than 10 mL/min. Thus, all kinetic data found were obtained under conditions where increased shear rate did not result in an increase in the interfacial rate (i.e., the rate of absorption/binding to the surface). In other words, the rate of analyte of interest (i.e., antibodies 130) transport was always greater than the observed adsorption or desorption rates.

Phosphate buffered saline (hereinafter "PBS"), pH 7.4 (Sigma Chemical Company, St. Louis, Mo.), and used as a buffer in all experiments unless otherwise stated. Bovine serum albumin (hereinafter "BSA", product No AA378, crystallized, greater than 97% purity), human $\gamma$-globulin (product number G-4386, electrophoretic purity approximately 99%), and fluorescein isothiocyanate (hereinafter "FITC") (isomer I, greater than 90% purity) used herein were also obtained from Sigma Chemical Company. The reagent for amination of the metal oxide surfaces, '(2-aminoethyl)-3-amino-propyl-trimethoxy-silane was obtained from United Chemical Technologies, Inc., Bristol, Pa. The biotinylation agent, 6-((biotinoyl)amino) hexanoic acid, succinimidyl ester, sodium salt (Sulfo-NHS-LC-Biotin); the streptavidin conjugate with a fluorescent label (Oregon Green 500) and a pH insensitive fluorescent label, BODIPY, ('(4,4-difluoro-5,7diphenyl4-bora-3a, 4a-diaza-s-indace-3-propionyl)-N'-iodo-acetyl-ethyleneamone were obtained from Molecular Probes, Inc., Eugene, Oreg. Anti-biotin antibodies (product number 31852), were obtained from Pierce, Rockford, Ill.

FITC labeled anti-biotin antibodies, IgG-FITC and y globulin-FITC conjugates were prepared following a modified procedure described by the inventors of the present invention in Asanov et al. *J. Colloid Interface Science*, 191 (1997). The antibody-BODIPY and $\gamma$-globulin-BODIPY conjugates were formed by dissolving a 5-fold molar excess of BODIPY in dimethylsulfoxide and 10 $\mu$L of BODIPY solution was mixed with about 1 mL of 1 mg/mL antibody solution in PBS. The labeling reactions were carried out for between about 30 and 50 minutes at room temperature (approximately 22° C.). The unreacted FITC or BODIPY was removed from the reaction mixtures by dialyzed the reaction mixtures in excessive amounts of PBS using dialysis cassettes purchased from Pierce. The conjugate solutions were stored at about 4° C. and used within 2 days of preparation. The molar ratios of FITC:$\gamma$-globulin, FITC:IgG, FITC:antibody, BODIPY:$\gamma$-globulins, BODIPY:IgG, and BODIPY:antibody were determined spectrophotometrically and ranged from between about 0.7 and 0.9. The streptavidin-Oregon Green conjugate was reconstituted in PBS from lyophilized powder as received.

The waveguide 104 was made from indium tin oxide ("ITO") film of optical quality obtained from Optical Components, Inc., Covina, Calif. The waveguide 104 was deposited directly on the planar translucent substrate 102 (i.e., a quartz slide) and was approximately 350 nm thick, with a resistivity of about 12 ohm/cm$^2$, a refractive index of between about 1.95 and 2.00, and a 9:1 In:Sn atomic composition, as specified by the manufacturer. The waveguide 104 on the substrate second surface 106 was divided by etching two separate sections of the waveguide 104 to form three areas (a working electrode area 162 and two auxiliary electrode areas 164a, 164b), as shown in FIG. 3.

The working electrode area 162 and auxiliary electrode areas 164a, 164b were prepared for biotinylation by treating them for 20 minutes in hot chromic acid (about 80 g/L K$_2$Cr$_2$O$_7$ in 96–98% sulfuric acid at about 70° C.), rinsing in deionized water, and soaking in about 2 M NaOH for at least about 24 hours. The working electrode area 162 and auxiliary electrode areas 164a, 164b were then rinsed with deionized water and air dried. Thereafter, adsorbed water was removed from the working electrode area 162 and auxiliary electrode areas 164a, 164b by drying them at about 115° C. for four hours. The working electrode area 162 and auxiliary electrode areas 164a, 164b were treated for several hours in a 10% solution of refluxing silane, under a nitrogen atmosphere. After amination, the working electrode area 162 and auxiliary electrode areas 164a, 164b were rinsed with water followed by rinsing with ethanol. Biotinylation of the working electrode area 162 and auxiliary electrode areas 164a, 164b was accomplished in 0.1 M sodium bicarbonate buffer, about pH 8.0, at room temperature (about 22° C.). The surfaces of the working electrode area 162 and auxiliary electrode areas 164a, 164b were exposed overnight to 1 mg/mL of the biotinylation agent, sulfo-NHS-LC-biotin. Cyclic voltammograms were obtained before and after amination and biotinylation reactions to verify surface modification (not shown).

It has been found that ITO transparent electrodes as waveguides 104 offers advantages over previously know waveguides due to its high refractive index (between about 1.9 and 2.0) which results in a thin planar optical waveguide 104 with multiple reflections of the light beams 134. The difference between refractive indexes of the substrate 102 (quartz slide—approximately 1.47) and waveguide 104 (ITO—approximately 2.0) yields a much smaller critical angle for total internal reflection (approximately 47.3°) and permits capture of the incident light between the quartz substrate 102 and the test sample solution (aqueous) (refractive index about 1.33) in contact with the waveguide 104. It has been found that waveguides 104 of thick ITO films (greater than 1 $\mu$m) effectively captured the light beams 134, as shown in FIG. 2. However, in order to minimize the number of parameters which affect TIRF sensitivity, thin ITO films providing a single reflection were used for all kinetic measurements.

It is known that a variety of modifications of metal oxide surfaces, such as ITO film, can be utilized to form biosensors. In the present example, a primary amine reactive group covalently attached to the surface through a spacer was chosen because of the need for further surface derivatization to create a platform for numerous types of biosensors.

Biotin was chosen because this relatively small antigen is well characterized and procedures for its covalent attachment are well known. Furthermore, polyclonal anti-biotin antibodies are commercially available. Additionally, biotin was chosen because biotinylation of the ITO waveguide surface incorporates the versatility of biotin-avidin technology. A variety of biological molecules are available commercially in the form of biotin or avidin conjugates along with biotin and avidin derivatives containing different reactive groups. However, as previously discussed, poor reversibility of the biotin-avidin bond limits application of this technology to single use devices. Nonetheless, it has been found that electrochemistry coupled with TIRF technology allows avidin-biotin interactions and allows electrochemical perturbation which promotes disruption of this complex without deterioration of the biosensor. Furthermore, electrochemistry provides additional analytical and preparative capacity to detect and to control interfacial biospecific and nonspecific interactions, as well as, to control different stages of the surface design assembly.

FIG. 4 illustrates cyclic voltammograms of bare and chemically modified ITO electrodes. Currents observed at between about +1.4 V and −0.9 V correspond to water electrolysis with oxygen and hydrogen evolution, respectively. For an untreated electrode (Curve 1), the cathodic wave between about −0.5 V and −0.8 V was diminished, but not eliminated following oxygen removal from the solution. Although no deterioration of optical properties of the ITO electrodes was observed with short-term cathodic polarization, prolonged polarization at less than −0.8 V resulted in reduction of the ITO electrodes which caused a mirror-like reflection unsuitable for TIRF use. However, alternating cathodic-anodic or prolonged anodic polarization did not degrade the optical properties of the ITO electrodes. Electrodes maintained original optical quality for more than one hundred hours of experimentation.

The zero charge point for $SnO_2$ electrodes is approximately +0.3 V at neutral pH (approximately 7.0). Since the electrochemical properties of ITO electrodes are close to that of $SnO_2$, the ITO electrode surface is likely positively charged at greater than about 0.3 V and negatively charged at less than about 0.3 V. Furthermore, it is known that, for $SnO_2$ electrodes, cathodic polarization increases hydrophobicity of the electrode surface. This is believed due to the reduction of the upper layer of the metal oxide to form either the zero valence metal or non-stoichiometric oxide which are both hydrophobic. Thus, electrochemical polarization changes the chemical composition of the electrode surface, as well as, affects the surface charge and the potential drop across the double electric layer ("DEL") (the interface between the electrode and electrolyte, one being "dense", the other being "diffuse"). At physiological ionic strength, the thickness of DEL (Debye screening length about 1.3 nm), is significantly less than the size of a globular protein, such as IgG (about 10 nm). As a result, adsorption behavior of large protein molecules can be relatively insensitive to net charges both of the protein and the electrode surface. Since hydrophobic interactions are a primary driving force for adsorption of globular proteins, changes of surface hydrophobicity upon electrochemical polarization affect adsorption more significantly than variations in electrostatic conditions.

As shown in FIG. 4, Curve 2, amination of ITO electrodes resulted in reduction of cathodic waves in the cyclic voltammograms with respect to untreated surfaces. Aminated electrodes revealed an additional reversible current wave at approximately −0.5 V. This wave can be attributed to the protonation of an amine surface moiety. Surprisingly, under cathodic polarization, aminated ITO electrodes were more stable than untreated ITO electrodes with respect to the oxide to metal film reduction. At a more basic pH (greater than about 8.6), cyclic voltammograms of aminated ITO electrodes did not exhibit this wave, as shown in FIG. 5, Curve 4. Additionally, biotinylated electrodes did not reveal this wave at either at basic or neutral pH, as shown in FIG. 5, Curve 5. The wave at about −0.5 V was also not observed for alkyl-treated ITO surfaces which did not contain the amine moiety, as shown in FIG. 4, Curve 3. Thus, the presence of a wave at approximately −0.5 V was used to verify the presence of a primary amine at the surface, while the absence of the wave after incubation with a biotinylation reagent was used as indirect evidence for surface biotinylation.

Figure 6:
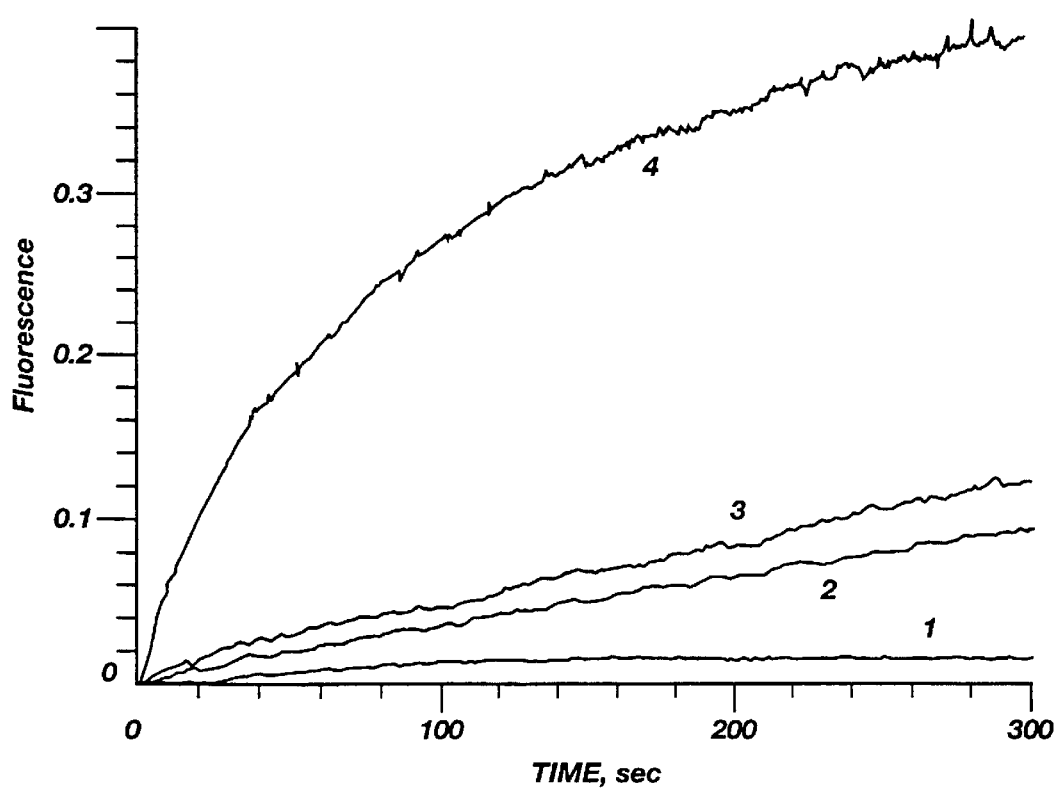
FIG. 6 illustrates the kinetics of nonspecific and specific interfacial binding of the present invention.

To distinguish the specific binding of an anti-biotin antibody to the surface-immobilized biotin from the nonspecific adsorption of antibodies, the antibody interactions were compared with nonspecific adsorption of IgG and γ-globulin. These comparisons were conducted without electrochemical polarization, under open circuit conditions. FIG. 6 illustrates the kinetics of nonspecific and specific interfacial binding (fluorescence intensity set forth in arbitrary units proportional to surface concentration of analyte). Over the same time interval, the nonspecific adsorption (Curves 1, 2 and 3) demonstrates lower affinity and slower kinetics than the attachment of anti-biotin antibodies to the biotinylated ITO surface (Curve 4). Untreated ITO surfaces (kinetics not shown) demonstrate higher adsorption affinity and faster kinetics for IgG and γ-globulin adsorption compared to either biotinylated or aminated surfaces.

The common method to minimize nonspecific adsorption is to treat the sensing surface with an agent which blocks the sites of nonspecific adsorption and which does not interfere with antibody-antigen interactions. It is known that BSA suppresses nonspecific adsorption in most immunoassay systems utilizing a polystyrene substrate. However, it has been found that for untreated ITO electrodes pre-adsorption or addition of 0.01 mg/mL BSA drastically reduced IgG and γ-globulin adsorption. In the case of aminated ITO electrodes, pre-adsorption of BSA or addition of 0.01 mg/mL BSA to the IgG and γ-globulin solutions resulted in suppression of nonspecific adsorption to approximately 3% of the specific binding. Since BSA effectively blocked sites of nonspecific interactions, all biospecific binding was conducted in the presence of 0.01 mg/mL BSA, unless otherwise noted.

Additionally, there is a kinetic criterion which can be used to discriminate specific and nonspecific interactions. Antibody-antigen and biotin-avidin interactions in this example exhibited faster binding kinetics than nonspecific adsorption. The difference in kinetics was used as a supplementary experimental factor to discriminate between nonspecific and specific interactions.

Association rates of antibody-antigen interactions have been shown to fall within a relatively narrow range between about $10^6$ and $10^7$ $M^1$ $s^{-1}$, while the dissociation rate constants for different antibody-antigen pairs differ by a factor of approximately $10^3$. Therefore, for the development of a reversible immunosensor, the dissociation lifetime, $t_d=1/K_d$, is a parameter of paramount importance. A true immunosensor requires that the system respond to any increase in analyte concentration, as well as, to any decrease. As previously noted, most of the immunosensors developed to date are actually detectors with "yes" or "no" response (i.e., whether the analyte of interest is present or not) rather than true sensors, since an antibody-antigen bond is typically too strong to allow rapid reversibility. The present invention has overcome this problem by developing immunosensors which are inherently reversible or which can be quickly regenerated in situ to detect a continuous stream of analyte of interest.

Figure 7:
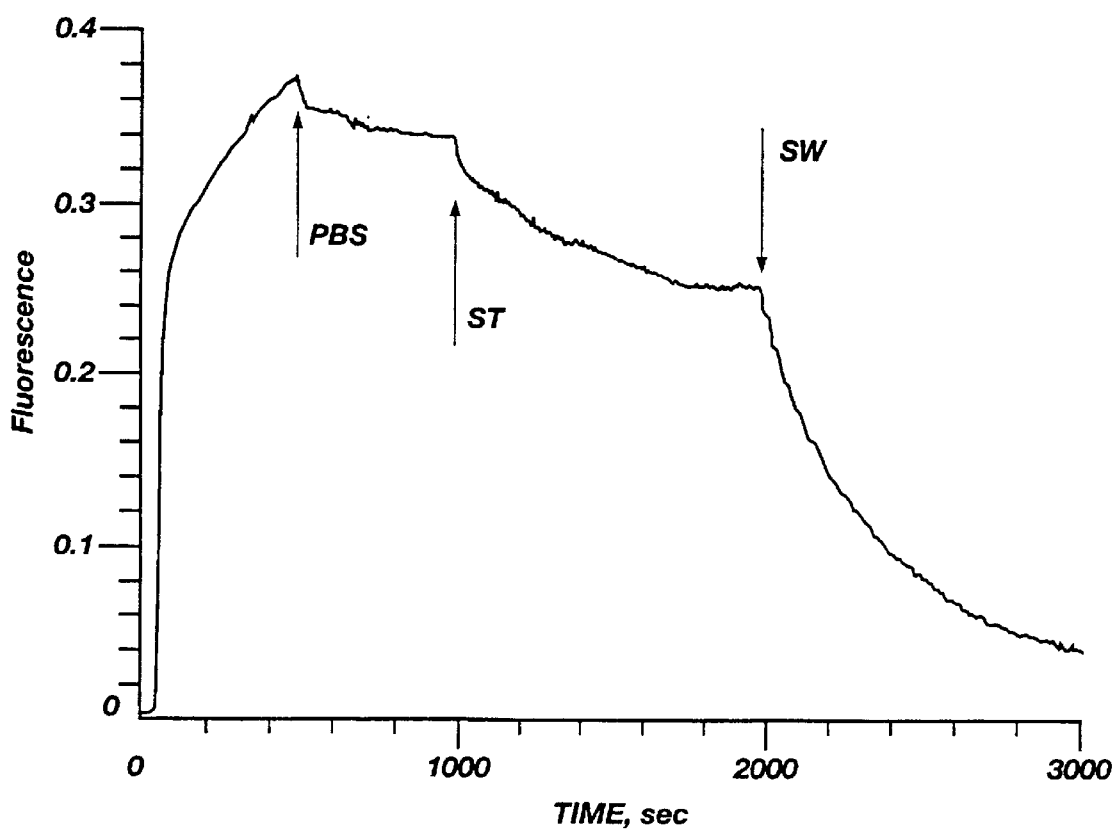
FIG. 7 illustrates the kinetics of specific antibody binding to a biotinylated ITO surface of the present invention.

FIG. 7 illustrates the typical kinetics of specific antibody binding to a biotinylated ITO surface (fluorescence intensity set forth in arbitrary units proportional to surface concentration of analyte). The observed kinetics of interfacial binding was non-Langmuir, comparable to logarithmic kinetics (Γ=k ln t), typical for heteroenergetic interactions. Dissociation kinetics also demonstrates heteroenergetics. By definition, the dissociation half-life is the period during which the signal decays by 50%. In the case of monoexponential kinetics, the half-life characterizes the entire decay process. However, in the case of "tailed" kinetics which is typical for heteroenergetic interactions, the time necessary for a complete regeneration may be significantly longer than the half-lifetime. In the present example, antibody-antigen and streptavidin-biotin interactions demonstrated heteroenergetic kinetics.

Figure 9:
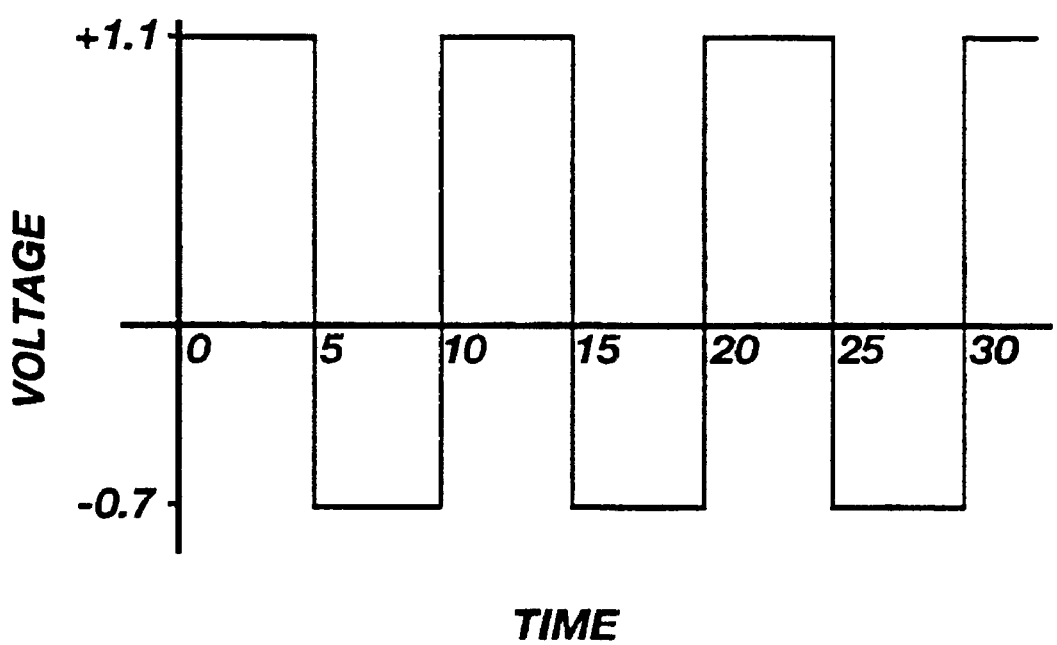
FIG. 9 illustrates a graph of a typical square wave polarization function of the present invetion.

In the absence of electrochemical polarization, the decrease of antibody surface concentration upon rinsing with a pure buffer was extremely slow, as shown in FIG. 7 in the time interval between about 500 and 1000 seconds. Under these conditions, the dissociation half-life was greater than about $10^5$ seconds, which is typical for high affinity antibodies. Application of cyclic electrode potential changes between about −0.7 V and +1.1 V, at the time interval between about 1000 and 2000 seconds, (a square wave polarization function) resulted in a notable increase in the rate of dissociation. The potential changes were maintained for between about 0.1 and 10 seconds during the cycling. FIG. 9 illustrates a typical square wave polarization function wherein the electrode potential is cycled between −0.7 V and +1.1 V for a time interval of 5 seconds between potential cycles. An estimated half-lifetime for this dissociation kinetics was less than about $10^4$ seconds. Surprisingly, the application of a square wave polarization function over the same voltage range (i.e., between about −0.7 V and +1.1 V), at the time interval between about 2000 and 3000 seconds, promoted dissociation more effectively and reduced the dissociation half-lifetime to about 300 seconds. It is, of course, understood that for different applications (i.e., different binding partners) may require different potential cycles which may or may not include a polarity shift between positive ("+") and negative ("−") voltages.

The first cycle of electrochemical regeneration of a freshly prepared biotinylated ITO surface reduced biospecific activity of the sensor surface to 20–25% of its original affinity. However, during the next ten regeneration cycles, the affinity decreased less than 10%. In fact, utilization of a square wave polarization treatment provided reproducible conditions at the biotinylated sensor surface, suitable for construction of a reusable immunosensor.

Figure 8:
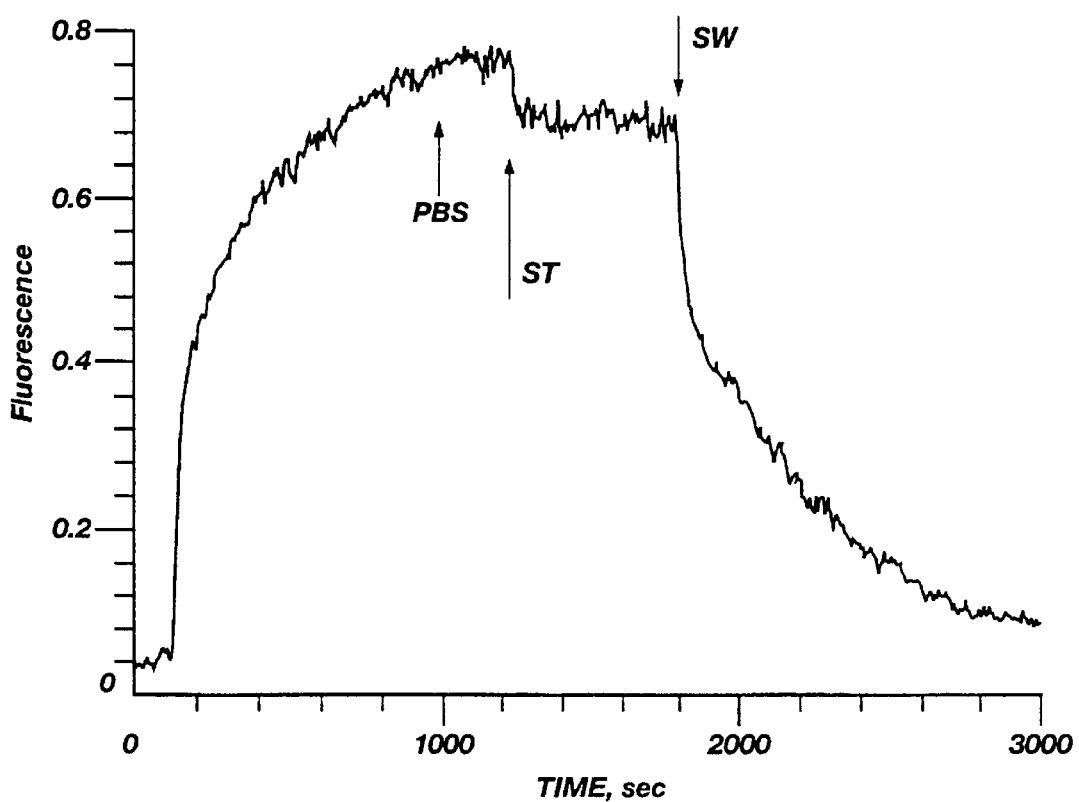
FIG. 8 illustrates the kinetics of biospecific interaction of streptavidin binding with a biotinylated surface and electrochemically stimulated dissociation of the surface complex of the present invention.

FIG. 8 illustrates the kinetics of the biospecific interaction of streptavidin binding with a biotinylated surface and electrochemically stimulated dissociation of the surface complex. As in the case of antibody-antigen interactions, streptavidin binding to a biotinylated surface is controlled by the interfacial kinetics. Untreated ITO surfaces exhibited relatively high affinities to streptavidin. However, amination of the ITO surface resulted in suppression of nonspecific adsorption to approximately 2% of the untreated surface affinity. Since it was believed that subsequent biotinylation of the aminated ITO surface could lead to an increase of nonspecific adsorption, the biospecific activity of streptavidin was blocked prior to adsorption by addition of an excess of biotin to the streptavidin solution. Adsorption of deactivated streptavidin was less than 3% of the TIRF signal which can be attributed to biospecific binding.

The interfacial biotin-streptavidin complex is extremely stable. No detectable desorption into circulating PBS was observed after streptavidin was bound to the biotinylated surface, as shown in FIG. 8 at the time interval between about 1000 and 1250 seconds. Application of a saw tooth electrochemical polarization function from −0.9 to +1.3 V resulted in a drop to approximately 90% of the original signal. This decrease was observed immediately following the initiation of polarization, as shown in FIG. 8 at the time interval between about 1250 and 1800 seconds. Prolonged electrochemical perturbation with the saw tooth polarization function had little, if any, affect on the streptavidin-biotin dissociation. Surprisingly, a square wave polarization over the same voltage rage resulted in a relatively fast dissociation with a half-life of approximately 200 seconds, as shown in FIG. 8 at the time interval between about 1800 and 3000 seconds. This electrochemical treatment ultimately led to a complete regeneration of the biotinylated surface. Binding-release cycles were repeated more than 30 times without significant loss of biospecific activity at the surface. Thus, electrochemically stimulated dissociation of streptavidin-biotin complexes demonstrates one of few examples of lability of the biotin-avidin bond.

Varying electrode polarization results in changes of a number of parameters in the double electric layer. These parameters include: sign and surface density of charges, intensity of the electric field in the dense and diffuse parts of the DEL, changes of the dielectric constant, variation of surface chemistry, and changes of ion concentrations in the DEL. Local changes of pH might affect FITC fluorescence which is known to be pH sensitive. Indeed, small back responses, typically within 5% variation of the TIRF signal, were observed for FITC conjugates under alternating electrochemical polarization. Test experiments conducted with a pH insensitive fluorescent label, BODIPY, gave close kinetic results and showed little or no effect of the label on the interfacial behavior of proteins used in this example.

This example demonstrates the capability of electrochemical polarization to regulate the antibody-antigen and avidin-biotin binding. This has resulted in a biosensor for simultaneous sensing and control of interfacial biospecific interaction by the application of electrochemistry along with a TIRF flowcell.

However, it is understood that the present invention is not limited to only TIRF flowcells. The described electrochemistry alone or in combination with selective surface chemistry can be used in various immunoassays where reversibility is a problem. The present invention can be incorporated with solid-phase peptide synthesis which provides a versatile tool for sensor surface design with biologically significant compounds. For example, short or long synthetic peptides which mimic native antigen epitopes and bind to antibodies with an affinity comparable to that of the native antigen, can be synthesized directly on the sensor surface and used for numerous clinical applications.

It is also possible to prepare epitopes by the solid phase method of Merrifield. Different solid supports and different strategies are known seen, e.g. Barany and Merrifield in *The Peptides, Analysis, Synthesis, Biology*, Vol. 2, E. Gross and J. Meienhofer, eds., (Acad. Press, N.Y., 1980), Kneib-Cordonier and Mullen *Int. J. Peptide Protein Res.*, 30, 705–739 (1987) and Fields and Noble *Int. J. Peptide Protein Res.*, 35, 161–214 (1990). The synthesis of compounds in which a peptide bond is replaced by an isostere, can, in general, be performed using well known protecting groups and activation procedures. Procedures to synthesize the modified isosteres are described in the literature e.g. for a —$CH_2$—NH— isostere and for a —CO—$CH_2$— isostere.

For example, suitably $N^\alpha$ protected (and side-chain protected if reactive side-chains are present) amino acid derivatives or peptides are activated and coupled to suitably carboxyl protected amino acid or peptide derivatives on a solid support. Protection of the α-amino functions generally takes place by urethane functions such as the acid-labile tertiary-butyloxycarbonyl group ("Boc"), benzyloxycarbonyl ("Z") group and substituted analogs or the base-labile 9-fluoremyl-methyloxycarbonyl ("Fmoc"). group. The Z group can also be removed by catalytic hydrogenation. Other suitable protecting groups include the Nps, Bmv, Bpoc, Aloc, MSC, etc. A good overview of amino protecting groups is given in *The Peptides, Analysis, Synthesis, Biology*, Vol. 3 E. Gross and J. Meienhofer, eds., (Academic Press, New York, 1981). Protection of carboxyl groups can take place by ester formation e.g. base-labile esters like methyl or ethyl, acid labile esters like tert. butyl or, substituted, benzyl esters or hydrogenolytically. Protection of side-chain functions like those of lysine and glutamic or aspartic acid can take place using the aforementioned groups. Protection of thiol, and although not always required, of guanidino, alcohol and imidazole groups can take place using a variety of reagents such as those described in *The Peptides, Analysis, Synthesis, Biology id*. or in *Pure and Applied Chemistry*, 59(3), 331–344 (1987). Activation of the carboxyl group of the suitably protected amino acids or peptides can take place by the azide, mixed anhydride, active ester, or carbodiimide method especially with the addition of catalytic and racemization-suppressing compounds like 1-N-N-hydroxybenzotriazole, N-hydroxysuccinimide, 3-hydroxy-4-oxo-3,4-dihydro-1,2,3,-benzotriazine, N-hydroxy-5norbornene-2,3-dicarboxyimide. Also the anhydrides of phosphorus based acids can be used. See e.g. *The Peptides, Analysis, Synthesis, Biology, supra* and *Pure and Applied Chemistry*, 59(3), 331–344 (1987).

In this and other regards, the aminated ITO TIRF-EC platform is not limited to naturally occurring molecules. Various amino acid sequences can be synthesized directly on a sensor surface and used for metal-ion coordination. Moreover, solid-phase peptide synthesis also facilitates combinatorial chemistry to construct a specifically desired surface receptor molecule.

Epitopes can be determined by the method of Geysen described in U.S. Pat. No. 5,194,392.

It is, of course, understood that although the above example focuses on a particular biological binding pairs, various biological binding partners, such as antigen-antibody, avidin-biotin, enzyme-substrate, cell receptor-substrate/analog, antibody/anti-antibody, DNA, RNA, and fragments thereof, may be utilized with the present invention. It is also understood that although the above example focuses on a fluorescence detection method for the assay, other methods, such as the use of radioactive tracers, may be employed.

Having thus described in detail preferred embodiments of the present invention, it is to be understood that the invention defined by the appended claims is not to be limited by particular details set forth in the above description, as many apparent variations are possible without departing from the spirit or scope thereof.

What is claimed is:

1. In an electrochemical method of disassociating a first biological binding partner from a corresponding second biological binding partner associated with a waveguide surface in an assay, said electrochemical method involving the application of electrical potential to said waveguide surface, the improvement comprising:

applying said electrical potential to the waveguide surface as a square wave polarization function to disassociate said first biological binding partner from said second biological binding partner.

2. The improvement of claim 1 wherein the waveguide surface is comprised of indium tin oxide.

3. The improvement of claim 1 wherein the biological binding partners are selected from the group consisting of antigen-antibody, avidin-biotin, enzyme-substrate, cell receptor-substrate/analog, antibody/anti-antibody, DNA, RNA, and fragments thereof.

4. The improvement of claim 3, wherein the corresponding second biological binding partner is an antigen comprised of an epitope.

5. The improvement of claim 4 wherein the epitope was produced by a solid phase peptide synthesis performed on said waveguide surface.

6. The improvement of claim 1 wherein said assay is selected from a group consisting of a spectroscopic assay and a radioactive tracer detection assay.

7. The improvement of claim 6 wherein spectroscopic assay is a spectrofluoroscopic assay.

8. The improvement of claim 7 wherein the spectrofluoroscopic assay is a total internal reflection fluorescence assay.

\* \* \* \* \*

UNITED STATES PATENT AND TRADEMARK OFFICE
CERTIFICATE OF CORRECTION

PATENT NO.    : 6,511,854 B1
DATED         : January 28, 2003
INVENTOR(S)   : Asanov et al.

It is certified that error appears in the above-identified patent and that said Letters Patent is hereby corrected as shown below:

Column 1,
Line 13, please add the header -- ACKNOWLEDGEMENT -- and the following lines:
-- This invention was made with U.S. Government support under Contract No. HER-9108767 awarded by the National Science Foundation/EPSCoR grant. The Government has certain rights in this invention. --

Signed and Sealed this

Tenth Day of August, 2004

JON W. DUDAS
*Acting Director of the United States Patent and Trademark Office*